(12) United States Patent
Park et al.

(10) Patent No.: US 9,498,774 B2
(45) Date of Patent: Nov. 22, 2016

(54) COMPOSITE BODY IN WHICH FIRST METAL-CONTAINING PARTICLES AND SECOND METAL-CONTAINING PARTICLES ARE SUPPORTED ON CARBON MATERIAL OR CONNECTED BY CARBON MATERIAL, AND METHOD FOR PRODUCING SAME

(71) Applicant: Korea Institute of Energy Research, Daejeon (KR)

(72) Inventors: Ji Chan Park, Daejeon (KR); Heon Jung, Daejeon (KR); Ho Tae Lee, Daejeon (KR); Jung Ii Yang, Daejeon (KR); Dong Hyun Chun, Daejeon (KR); Sung Jun Hong, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 0 days.

(21) Appl. No.: 14/740,530

(22) Filed: Jun. 16, 2015

(65) Prior Publication Data

US 2015/0298114 A1    Oct. 22, 2015

Related U.S. Application Data

(63) Continuation-in-part of application No. PCT/KR2013/009723, filed on Oct. 30, 2013.

(30) Foreign Application Priority Data

Dec. 17, 2012 (KR) ........................ 10-2012-0147508

(51) Int. Cl.
*B01J 35/00* (2006.01)
*C07F 3/02* (2006.01)
(Continued)

(52) U.S. Cl.
CPC ........... *B01J 35/0073* (2013.01); *B01J 23/745* (2013.01); *B01J 23/75* (2013.01);
(Continued)

(58) Field of Classification Search
CPC .. B01J 35/0073; B01J 35/023; B01J 23/745; B01J 23/755; B01J 23/70; B01J 23/75; B01J 23/76; B01J 37/0201; B01J 37/0036; B01J 37/04; B01J 37/08; B01J 37/16; B01J 37/088

USPC .................................. 502/182–185

See application file for complete search history.

(56) References Cited

U.S. PATENT DOCUMENTS 8,962,703 B2 *   2/2015   Park ........................ C07C 1/044
                                                              502/177
2010/0266478 A1 *  10/2010  Kim ........................ B01J 21/04
                                                              423/447.1

(Continued)

FOREIGN PATENT DOCUMENTS

EP          1952885 A1      8/2008
JP          2003313011 A    11/2003

(Continued)

OTHER PUBLICATIONS

Eggenhuisen, Tamara M. et al., Fundamentals of Melt Infiltration for the Preparation of Supported Metal Catalysts. The Case of Co/SiO2 for Fischer-Tropsch Synthesis, J. Am. Chem. Soc. 2010, vol. 132, pp. 18318-18325 (8 pages).

(Continued)

*Primary Examiner* — Patricia L Hailey
(74) *Attorney, Agent, or Firm* — Osha • Liang LLP

(57) ABSTRACT

The present invention relates to a composite body in which first metal-containing particles and second metal-containing particles are supported on a carbon material or connected by a carbon material, and a method for producing the same. The above composite body can, if the first metal-containing particles exhibit a catalytic activity, be applied as a reaction catalyst and can also be used in various fields such as the manufacture of the adsorbent or the separation membrane.

20 Claims, 8 Drawing Sheets

(51) Int. Cl.
*B01J 37/04* (2006.01)
*B01J 37/08* (2006.01)
*B01J 23/76* (2006.01)
*B01J 23/745* (2006.01)
*B01J 23/75* (2006.01)
*B01J 23/755* (2006.01)
*B01J 35/02* (2006.01)
*B01J 37/00* (2006.01)
*B01J 37/02* (2006.01)
*B01J 23/70* (2006.01)
*B01J 37/16* (2006.01)
*B01J 35/10* (2006.01)

(52) U.S. Cl.
CPC ............ *B01J 23/755* (2013.01); *B01J 23/76* (2013.01); *B01J 35/006* (2013.01); *B01J 35/0013* (2013.01); *B01J 35/023* (2013.01); *B01J 37/0018* (2013.01); *B01J 37/0036* (2013.01); *B01J 37/0201* (2013.01); *B01J 37/04* (2013.01); *B01J 37/08* (2013.01); *B01J 37/088* (2013.01); *C07F 3/02* (2013.01); *B01J 23/70* (2013.01); *B01J 35/1028* (2013.01); *B01J 35/1038* (2013.01); *B01J 35/1042* (2013.01); *B01J 35/1061* (2013.01); *B01J 37/023* (2013.01); *B01J 37/084* (2013.01); *B01J 37/16* (2013.01)

(56) References Cited

U.S. PATENT DOCUMENTS

| | | | |
|---|---|---|---|
| 2012/0115715 A1* | 5/2012 | Wolters | B01J 23/75 502/240 |
| 2012/0245022 A1 | 9/2012 | Weiner et al. | |
| 2016/0083410 A1* | 3/2016 | Park | C01G 49/04 502/185 |

FOREIGN PATENT DOCUMENTS

| | | |
|---|---|---|
| KR | 20040104239 A | 12/2004 |
| KR | 100778071 B1 | 11/2007 |
| KR | 20090037059 A | 4/2009 |
| KR | 20110090400 A | 8/2011 |
| KR | 20110097197 A | 8/2011 |
| KR | 20120019524 A | 3/2012 |

OTHER PUBLICATIONS

International Search Report issued in PCT/KR2013/009723, mailed Feb. 10, 2014 (3 pages).

* cited by examiner

COMPOSITE BODY IN WHICH FIRST METAL-CONTAINING PARTICLES AND SECOND METAL-CONTAINING PARTICLES ARE SUPPORTED ON CARBON MATERIAL OR CONNECTED BY CARBON MATERIAL, AND METHOD FOR PRODUCING SAME

TECHNICAL FIELD

The present invention relates to a composite body in which first metal-containing particles and second metal-containing particles are supported on a carbon material or connected by a carbon material, and a method for producing the same.

The above composite body can, if the first metal-containing particles exhibit a catalytic activity, be applied as a reaction catalyst and can also be used in various fields such as the manufacture of an adsorbent or a separation membrane.

BACKGROUND ART

Conventionally, a supported catalyst using metal oxides as a support has been prepared by a method in which a metal salt solution was slowly dropped in the metal oxide support synthesized at a pre-formed commercial or laboratory level and then subjected to drying and supporting.

However, according to the above conventional method, the pore volume and the effective surface area of the metal oxide support have limited the amount of metal salt that can be uniformly supported on the metal oxide support.

To overcome the above-described problems recently, there were made studies for uniformly supporting a nano-catalyst on the surface of carbon materials through an incipient wet impregnation method and a repeated oxidizing and calcining process, but in the course of the preparation, the catalyst was prepared through the incipient wet impregnation method and the repeated oxidizing and calcining process, and thus there were disadvantages in that the preparation procedures are complicated (see, Korean Patent Application Laid-open No. 10-2012-0019524).

If a high concentration of salt is supported on a metal oxide support with small pores using a conventional wet impregnation method, it would take a long time. If a metal salt is supported by the melt impregnation process which has been developed recently, the metal salt can be more easily supported on the support in a well-dispersed state. However, since such a method also uses the pre-formed metal oxide support, the amount of salt that can be ultimately supported is limited (see, de Jong et al., J. Am. Chem. Soc., 2010, 132, 18318-18325).

In the traditionally known supporting method including the above-mentioned method, it was difficult to support metal particles on the support structure at a high concentration. Especially when supporting the particles at a high concentration, it caused a problem in that the size of particles was increased and the stability was decreased.

In order to ensure a high dispersibility and stability of the particles, complicated processes are required for synthesizing the advantageous support in the dispersibility and stability or the catalytic reaction must be restrictively conducted under a low temperature of 200° C. or less. However, these methods have problems such as a limited pore volume of the support, and an influence of the support, which occupies much weight and space, upon calcination. Although it is possible to apply a substance with a very large pore volume in order to solve these problems, this is not a fundamental solution.

PRIOR ART DOCUMENTS

Patent Document 1) Korean Patent Registration No. 10-00778071 (Nov. 28, 2007)
(Patent Document 2) Korean Patent Application Laid-open No. 10-2012-0019524 (Mar. 7, 2012)
(Patent Document 3) Korean Patent Application Laid-open No. 10-2009-0037059 (Apr. 15, 2009)
(Patent Document 4) Korean Patent Application Laid-open No. 10-2011-0090400 (Aug. 10, 2011)
(Patent Document 5) Korean Patent Application Laid-open No. 10-2004-0104239 (Dec. 10, 2004)

DISCLOSURE

Technical Problem

An object of the present invention is to provide a composite body in which metal-containing catalyst particles are uniformly supported at a high concentration, aggregation between the particles is prevented during a high temperature catalytic reaction to exhibit a high activity and stability, the metal-containing catalyst particles can be maintained at intervals between particles by the metal oxide particles for support, and the metal-containing catalyst particles and the metal oxide particles for support have been supported or connected by a carbon material.

Technical Solution

A first embodiment of the present invention provides a method for preparing a composite body in which first size-controlled metal-containing particles and second size-controlled metal-containing particles are supported on a carbon material or connected by a carbon material, the method comprising the following steps:

a first step of mixing a first metal hydrate salt forming a first metal oxide, a second metal hydrate salt forming a second metal oxide, and porous carbon material particles;

a second step of melt-infiltrating the first metal hydrate salt and the second metal hydrate salt in the pores of the porous carbon material particles at a temperature that can melt the first metal hydrate salt and the second metal hydrate salt;

optionally, a third step of drying the porous carbon material particles in which the first metal hydrate salt and the second metal hydrate salt are melt-infiltrated;

a fourth step of of subjecting the resultant carbon material particles to high temperature calcination at a temperature and condition that thermally decompose the first metal hydrate salt, the second metal hydrate salt and the porous carbon material, thereby forming the first metal oxide particles and the second metal oxide particles in which the particle sizes are controlled by the pores of the porous carbon material, while forming a composite body in which the first metal oxide particles and the second metal oxide particles are supported or connected by the carbon material remaining after the thermal decomposition of the porous carbon material; and optionally, a fifth step of chemically changing the first metal oxide particles, the second metal oxide particles or both of them to the first metal-containing particles or the second metal-containing particles.

A second embodiment of the present invention provides a composite body, prepared by the method of the above-described first embodiment, in which first metal-containing particles and second metal-containing particles are supported on a carbon material or connected by a carbon material, wherein the first metal-containing particles are maintained at intervals between the particles by the second metal-containing particles and the carbon material, and the first metal-containing particles are contained in an amount of 10 to 50% by weight, the second metal-containing particles are contained in an amount of 10 to 50% by weight, and the residual carbon material is contained in an amount of 20 to 60% by weight, based on the total amount of the composite body.

In the composite body according to the present invention, the first metal-containing particles may exhibit a catalytic activity and the second metal-containing particles can be inert to the catalytic reaction.

Moreover, in the composite body according to the present invention, the first metal-containing particles may be those in which the surface or the whole of the first metal oxide particles are reduced to the first metal.

Further, in the composite body according to the present invention, the first metal-containing particles may be a crystalline form having a grid structure, and the second metal-containing particles can be amorphous.

Hereinafter, the present invention will be described in detail.

The conventional methods for preparation of the supported catalyst have problems such as a limited pore volume of a support, and an influence of the support, which occupies much weight and space, upon calcination.

Accordingly, in order to solve these problems, the present invention provides a composite body in which the metal-containing catalyst particles can be maintained at intervals between particles by the metal oxide particles, which are composed of material used conventionally as the support, and the metal-containing catalyst particles and the metal oxide particles for support are supported on a carbon material or connected by a carbon material, so that the metal-containing catalyst particles are uniformly supported at a high concentration, and aggregation between the particles is prevented during a high temperature catalytic reaction to exhibit a high activity and stability.

The method of the present invention for preparing a composite body in which first second size-controlled metal-containing particles and second second size-controlled metal-containing particles are supported on a carbon material or connected by a carbon material, comprises the following steps:

a first step of mixing a first metal hydrate salt forming a first metal oxide, a second metal hydrate salt forming a second metal oxide, and porous carbon material particles;

a second step of melt-infiltrating the first metal hydrate salt and the second metal hydrate salt in the pores of the porous carbon material particles at a temperature that can melt the first metal hydrate salt and the second metal hydrate salt;

optionally a third step drying the porous carbon material particles in which the first metal hydrate salt and the second metal hydrate salt are melt-infiltrated;

a fourth step of subjecting the resultant carbon material particles to high temperature calcination at the temperature and condition that thermally decompose the first metal hydrate salt, the second metal hydrate salt and the porous carbon material, thereby forming the first metal oxide particles and the second metal oxide particles in which the particle sizes are controlled by the pores of the porous carbon material, while forming a composite body in which the first metal oxide particles and the second metal oxide particles are supported or connected by the carbon material remaining after thermal decompositon of the porous carbon material; and optionally a fifth step of chemically changing the first metal oxide particles, the second metal oxide particles or both of them to the first metal-containing particles or the second metal-containing particles.

At this time, each of the first metal-containing particles and the second metal-containing particles may independently be the first metal oxide particles and the second metal oxide particles. Alternatively, each of the first metal oxide particles and/or the second metal oxide particles may independently be changed to the first metal-containing particles or the second metal-containing particles by a chemical change such as a reduction. In this case, the chemical change can occur at the surface or the whole of the metal oxide particle.

The method of the present invention can prepare a composite body in which the first metal-containing particles and the second metal-containing particles are supported on a carbon material or connected by a carbon material, wherein the first metal-containing particles are maintained at intervals between particles by the second metal-containing particles and the carbon material, and wherein the first metal-containing particles are contained in an amount of 10 to 50% by weight, the second metal-containing particles are contained in an amount of 10 to 50% by weight, and the residual carbon material is contained in an amount of 20 to 60% by weight, based on the total amount of the composite body.

In accordance with the present invention, the first metal hydrate salt and the second metal hydrate salt are melt-infiltrated into the pores of the porous carbon material and then subjected to high temperature calcination, by which a large quantity of carbon is thermally decomposed and removed from the porous carbon material used as a soft-template in the formation of the first metal oxide particles and the second metal oxide particles, and at the same time the second metal hydrate salt is thermally decomposed to form the second metal oxide particles, and further the first metal oxide particles and/or the first metal-containing particles, which may exhibit a catalytic activity, are separated by the second metal oxide particles and thus a composite body containing those particles uniformly supported on the carbon material controlled in a small amount can be obtained quickly in various forms.

Also, upon preparation of the composite body according to the present invention, in the fourth step of subjecting the resultant carbon material particles to high temperature calcination at a temperature and condition that thermally decompose the first metal hydrate salt, the second metal hydrate salt and the porous carbon material, the first metal oxide particles are separated by the second metal oxide particles, thus inhibiting sintering of the first metal oxide particles and thus inhibiting aggregation between the first metal oxide particles.

Moreover, in the composite body of the present invention in which the first metal oxide particles and/or the first metal-containing particles, which exhibit a catalytic activity, are supported at a high concentration and highly dispersed, rapid diffusion of the reactants can be made on the surface of the first metal oxide particles and/or the first metal-containing particles, thereby being advantageous in terms of the contact efficiency.

Further, in accordance with the present invention, the first metal oxide particles and/or the first metal-containing particles exhibiting a catalytic activity are separated by the second metal oxide particles and thus aggregation between the particles can be prevented during the high temperature catalytic reaction, to thereby exhibit a high activity and stability.

In addition, in accordance with the present invention, the first metal oxide particles and/or the first metal-containing particles can improve their performance through the interaction with the second metal oxide particles and/or the second metal-containing particles and/or the interaction with the residual carbon material.

Accordingly, the composite body of the present invention can be applied to various fields such as the preparation of an absorbent or a separation membrane as well as a catalyst.

The porous material is divided into microporous and mesoporous materials depending on the pore size of the material. Usually, a pore size of 2 nm or less is called microporous, and a pore size of 2 to 50 nm is called mesoporous. The porous carbon material of the present invention is not limited by the size of the pores, but it is preferably a mesoporous carbon material for the production of metal-containing particles at a nano-level.

The porous carbon material particles preferably have a pore volume of 0.3 $cm^3$/g or more.

Non-limiting examples of the porous carbon material include activated carbon, activated charcoal, synthetic porous carbon support CMK, mixtures thereof and the like.

The average size of the porous carbon material particle may be on a micrometer scale, such as 200 nm to 0.2 μm. By adjusting the size of the porous carbon material particles, it is possible to adjust the size of the composite body which is a final product.

Meanwhile, the metal hydrate salt is a metal source having a lower melting point than the metal oxide which is usually used as a support. The examples of the metal hydrate salts and their melting points which can be used in the present invention are shown in Table 1 below.

TABLE 1

| Metal hydrate salt | Melting point (° C.) | Metal hydrate salt | Melting point (° C.) |
|---|---|---|---|
| $Mg(NO_3)_2 \cdot 6H_2O$ | 88.9 | $CrCl_3 \cdot 6H_2O$ | 83 |
| $Al(NO_3)_3 \cdot 9H_2O$ | 72.8 | $CaCl_2 \cdot 6H_2O$ | 45 |
| $Cr(NO_3)_3 \cdot 9H_2O$ | 60.06 | $MnCl_2 \cdot 4H_2O$ | 58 |
| $Ca(NO_3)_2 \cdot 4H_2O$ | 42.7 | $FeCl_3 \cdot 6H_2O$ | 37 |
| $ZnSO_4 \cdot 6H_2O$ | 70 | $CoCl_2 \cdot 6H_2O$ | 86 |
| $Fe(NO_3)_3 \cdot 9H_2O$ | 47.2 | $CuCl_2 \cdot 2H_2O$ | 100 |
| $Co(NO_3)_2 \cdot 6H_2O$ | 55 | $Al_2(SO_4)_3 \cdot 18H_2O$ | 86 |
| $Ni(NO_3)_2 \cdot 6H_2O$ | 56.7 | $Cr_2(SO_4)_3 \cdot 12H_2O$ | 90 |
| $Sr(NO_3)_2 \cdot 4H_2O$ | 100 | $FeSO_4 \cdot 7H_2O$ | 70 |
| $Zn(NO_3)_2 \cdot 3H_2O$ | 45.5 | $CoSO_4 \cdot 7H_2O$ | 74 |
| $Zn(NO_3)_2 \cdot 6H_2O$ | 36.4 | $NiSO_4 \cdot 6H_2O$ | 53 |

Each of the first metal hydrate salt and the second metal hydrate salt used herein independently have a melting point of 30 to 100° C.

Non-limiting examples of the first metal hydrate salt capable of being used as the precursor of the first metal oxide particles and/or the first metal-containing particles which can exhibit a catalytic activity, may include $Cr(NO_3)_3 \cdot 9H_2O$, $Fe(NO_3)_3 \cdot 9H_2O$, $Co(NO_3)_2 \cdot 6H_2O$, $Ni(NO_3)_2 \cdot 6H_2O$, $Pd(NO_3)_2 \cdot 2H_2O$, $FeCl_3 \cdot 6H_2O$, $CoCl_2 \cdot 6H_2O$, $CuCl_2 \cdot 2H_2O$, $Cr_2(SO_4)_3 \cdot 12H_2O$, $FeSO_4 \cdot 7H_2O$, $CoSO_4 \cdot 7H_2O$, $NiSO_4 \cdot 6H_2O$ and the like.

Meanwhile, non-limiting examples of the second metal hydrate salt capable of being used as the precursor of the second metal oxide particles and/or the second metal-containing particles which can act as an inert support for a catalytic reaction may include $Mg(NO_3)_2 \cdot 6H_2O$, $Al(NO_3)_3 \cdot 9H_2O$, $Zn(NO_3)_2 \cdot 3H_2O$, $Zn(NO_3)_2 \cdot 6H_2O$, $MnCl_2 \cdot 4H_2O$, $Al_2(SO_4)_3 \cdot 18H_2O$, $ZnSO_4 \cdot 6H_2O$, $ZrO(NO_3)_2 \cdot 6H_2O$ and the like.

The first step of mixing the first metal hydrate salt, the second metal hydrate salt and the porous carbon material particles is preferably conducted by mechanically grinding them.

Furthermore, if they are mixed without solvent (solvent free) to form a mixed powder, it is advantageous for high dispersion of the particles because dilution due to the solvent does not occur.

Meanwhile, the second step of melt-infiltrating the first metal hydrate salt and the second metal hydrate salt in the pores of the porous carbon material particle is procedurally easy and ultimately advantageous for high dispersion of the particles.

Metal hydrate salts have the values of their specific densities, respectively. The consideration of the density of the metal hydrate salt and the pore volume of the porous carbon material allows the salts to be more uniformly infiltrated.

Accordingly, the above metal hydrate salts are added in consideration of the density of each metal salt and the pore volume of the porous carbon material used. For the uniformity of the particles formed, the first metal hydrate salt and the second metal hydrate salt are preferably molten and infiltrated in an amount of 0.3 to 3 grams per the carbon unit gram thereof.

The melt-infiltration process can be conducted at a temperature near a melting point of the mixed salt. The exact melting point of the mixed hydrate salt can be seen through DSC (differential scanning calorimetry) analysis. More easily, the mixed salt can be infiltrated based on the salt having a high melting point.

In order to dissolve and better support a metal hydrate salt, it is important to adjust the temperature and maintain the pressure within the reaction vessel. It is also desirable that the reaction is conducted in a closed system so that the pressure due to the vapor pressure generated during the reaction does not disappear. The reaction time is about 4 to 48 hours and preferably about 24 to 48 hours so that the salts can be sufficiently entered into the inner pores.

The reactor used for the melt-infiltration is preferably a plastic vessel made of polypropylene or Teflon. This is because it is transparent, easily observed and convenient for mass production.

Before calcination, it is possible to dry the porous carbon material particles infiltrated with the first metal hydrate salt and the second metal hydrate salt. In this case, the drying can be conducted at a room temperature or it can be conducted at a temperature of 50 to 70° C.

Meanwhile, in the fourth step of subjecting the resultant carbon material particles to high temperature calcination at a temperature and condition that thermally decompose the first metal hydrate salt, the second metal hydrate salt and the porous carbon material, the first metal hydrate salt and the second metal hydrate salt are thermally decomposed to form the first metal oxide particles and the second metal oxide particles individually therefrom, and upon formation of the metal oxide particles, a large amount of carbon material used as a template is removed. At this time, the porous carbon material is thermally decomposed through the fourth step to obtain a composite body in which the first metal oxide particles and the second metal oxide particles are uniformly supported or connected by the residual carbon material.

In order to decompose the composite metal salt hydrates supported on the porous carbon materials and remove some carbon, the process for subjecting to high calcination under an air or oxygen condition is necessary. The heat treatment temperature can be applied from 200° C. or more which is when decomposition begins for the metal salts. When subjecting to calcination at a temperature of 700° C. or more, particle aggregation which is not suitable for use as a catalyst at a later time seriously occurs and so preferably the temperature between 300° C. and 650° C. is suitable.

The calcination is preferably conducted under the atmosphere, in consideration of cost issues and stability, but it is also possible to use pure oxygen and mixed oxygen in an attempt to ensure high reliability.

The calcination time has an influence on the amount of carbon to remove, and thus can be selected depending on the supported amount of the desired final metal-containing particles.

Non-limiting examples of the calcination time can be 1 to 24 hours. The heat treatment time can slightly vary depending on the calcination device. However, the carbon begins to be removed in earnest within one hour, and the majority of the carbon present in an excess amount is removed after the lapse of more than 24 hours. Accordingly, additional heat treatment has no great significance, but rather will be able to cause aggregation between particles.

In the fourth stage, the size of the first metal oxide particles and/or the second metal oxide particles can be variously adjusted to 2 to 30 nm depending on the calcination atmosphere.

On the other hand, the second metal oxide particles can be amorphous. Non-limiting examples of the second metal oxide can be silica, alumina, titania, zirconia or a mixture thereof.

In accordance with the present invention, the first metal-containing particles can be a metal or a metal oxide. Specifically, these particles may be nickel oxide, cobalt oxide, iron oxide, nickel metal, cobalt metal, iron metal, or a mixture thereof, but are not limited thereto.

If a reduction potential of the second metal oxide is higher than a reduction potential of the first metal oxide, the first metal oxide can be reduced to a first metal by a reduction reaction. The above reduction reaction can occur in the whole or a surface of the particle.

In the composite body of the present invention, the content of the first metal oxide particles and/or the first metal-containing particles may range from 10 to 80% by weight by controlling the content of the second metal oxide particles and/or the second metal-containing particles to be mixed and used. More preferably, in consideration of the high dispersion, the first metal oxide particles and/or the first metal-containing particles can be added in an amount of less than 50% by weight, and the second metal oxide particles and/or the second metal-containing particles can be added in an amount of greater than 10% by weight.

Preferably, the first metal oxide particles and/or the first metal-containing particles comprise 10 to 50% by weight of the composite body, the second metal oxide and/or the second metal-containing particles comprise 10 to 50% by weight of the composite body and the residual carbon comprises 20 to 60% by weight of the composite body, so that the first metal oxide particles and/or the first metal-containing particles are configurized to maintain a certain intervals between particles by the second metal oxide particles and/or the second metal-containing particles and the residual carbon material and retain an excellent activity.

In the composite body of the present invention, various metals and metal oxide nano-particles which can applied to catalysts, electrode materials, sensor materials, adsorption materials and the like are selectively uniformly dispersed as the first metal-containing particles on the carbon material. Accordingly, the composite body of the present invention can be used as catalysts, electrode materials, sensor materials, adsorption materials and the like.

In particular, if the metal or metal oxide nanoparticles dispersed as the first metal-containing particles are used as a catalyst, the composite body of the present invention may have advantageous benefits in the diffusion of the reactants when applied to the gas phase and the liquid phase catalytic reaction, and further it can obtain excellent reaction results even under a strict catalytic reaction environment while being stable at a high temperature. Specifically, in a high temperature reaction of greater than 200° C., such as a Fischer-Tropsch synthesis reaction which can cause a big problem due to very severe reaction heat, a local hot spot can be formed during the reaction, but the nanoparticle catalysts (corresponding to the first metal-containing particle) are separated by the second metal-containing particles and thus it is possible to solve problems such as aggregation of adjacent nanoparticle catalysts.

The above nanoparticle catalysts can be a metal or a metal oxide as defined in the composite body, particularly nickel oxide, cobalt oxide, and iron oxide or a mixed metal oxide or a partially or wholly reduced form thereof.

For example, when containing nickel oxide as the nanoparticle catalyst, it can be used as an oxidation catalyst or a hydrogenation catalyst for carbon monoxide or hydrocarbons. When containing a cobalt oxide as the nanoparticle catalyst, it can be used as a low temperature carbon monoxide oxidation catalyst. When containing iron oxide as the nanoparticle catalyst, it can be used as a catalyst for Fenton oxidation treatment.

When the first metal-containing particle is used as a nano-electrode active material particle, it can be specifically nickel oxide, cobalt oxide, iron oxide or a complex metal oxide thereof.

For example, when containing a nickel oxide as a nano-electrode active material particle, the composite body of the present invention can be used as an electrode material of a fuel cell. When containing a cobalt oxide as a nano-electrode active material particle, it can be used as an electrode material for a supercapacitor. When containing an iron oxide as a nano-electrode active material particle, it can be used as an electrode material for a solar cell.

When the composite body of the present invention is used as a sensor material, the first metal-containing particles may be a metal or a metal oxide such as nickel oxide, cobalt oxide, iron oxide or a complex metal oxide. For example, when including a nickel oxide as the nano-sensor particle, it can be used a gas sensor. When including a cobalt oxide as the nano-sensor particle, it can be used as an oxygen sensor or an optochemical sensor. When including an iron oxide as the nano-sensor particle, it can be used as a DNA sensor.

If the composite body of the present invention is used as an adsorbent, the first metal-containing particles can be a metal or a metal oxide such as nickel oxide, cobalt oxide, iron oxide or a composite metal oxide thereof. For example, when containing iron oxide as the nano-adsorbent particle, the composite body of the present invention can be used as an adsorbent material for treating contaminants, preferably organic contaminants, in the water treatment process.

Advantageous Effects

According to the present invention, in a composite body, the metal-containing catalyst particles can be maintained at intervals between particles by the metal oxide particles, which are composed of material which has been used conventionally for a support, and the metal-containing catalyst particles and the metal oxide particles have been supported or connected by the carbon material, accordingly the metal-containing catalyst particles are uniformly supported at a high concentration and aggregation between particles is prevented during a high temperature catalytic reaction to exhibit a high activity and stability.

BEST MODE

Hereinafter, the present invention will be described in more detail by way of examples and comparative examples. These examples are only intended to illustrate the present invention, and the scope of the present invention should not be construed as being limited to these examples.

Example 1

Synthesis of a Carbon-Based Catalyst in which Nickel is Supported on Alumina Utilizing Activated Charcoal As one of the candidates of the carbon materials used as a soft template for obtaining a highly dispersed catalyst, commercial activated charcoal (DARCO®, −100 mesh particle size, powder) was selected, and the analysis of the surface area and pores was conducted via nitrogen adsorption and desorption experiments. As a result, the value of BET SSA (specific surface area) was 1010 $m^2$/g and the pore volume was 0.85 $cm^3$/g.

First, 4.35 g of $Ni(NO_3)_2 6H_2O$ (Aldrich ≥97.5%, m.p.=56° C., fw=290.79 g/mol) salt and 3.65 g of $Al(NO_3)_3 \cdot 9H_2O$ (Aldrich ACS reagent, ≥98%, m.p.=72.8° C., fw=375.13 g/mol) salt were uniformly ground along with 5.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 70° C., stored for 24 hours and melt-infiltrated.

After aging for 24 hours, the mixed powder was cooled and dried at room temperature. Heat treatment was then conducted in a calcination oven in an air atmosphere at 400 to 600° C. for 4 hours, to remove excess carbon and decompose the infiltrated metal hydrate salt. Accordingly, it was possible to obtain the nickel/alumina/carbon-containing composite body in which NiO was supported on amorphous alumina and residual carbon.

Figure 1:
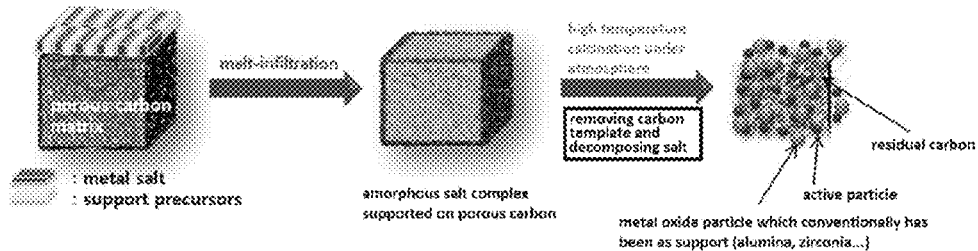
FIG. 1 is a schematic diagram of a method for preparing a composite body according to one embodiment of the present invention.
Figure 2:
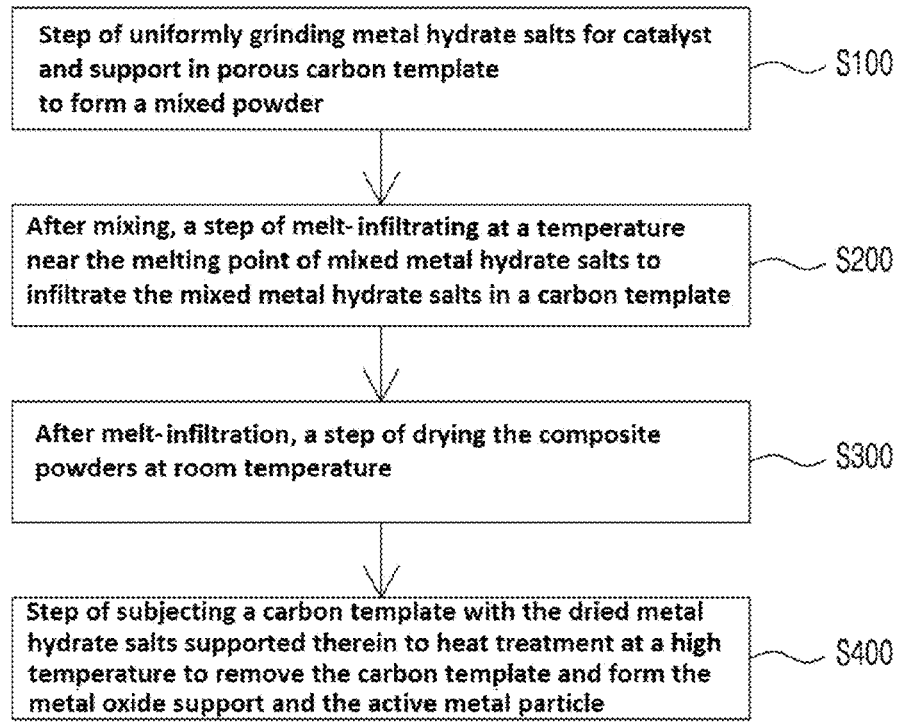
FIG. 2 is a manufacturing process chart of the composite body according to one embodiment of the present invention.
Figure 3:
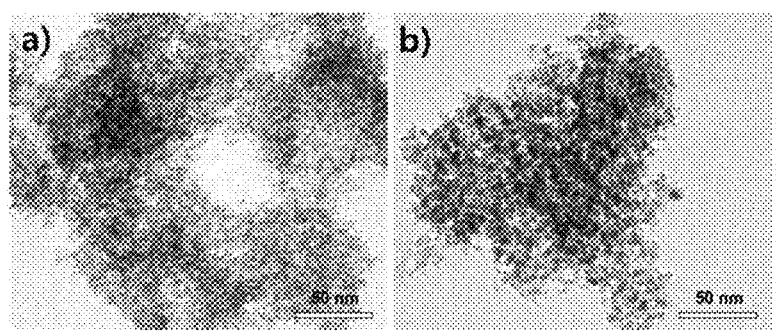
FIG. 3 is TEM images of a nickel/alumina/carbon-containing composite body by calcination temperature according to Example 1 of the present invention (a) calcination at 400° C. for 4 hours, and b) calcination at 500° C. for 4 hours.

FIG. 3 is TEM (transmission electron microscopy) images of the nickel/alumina/carbon-containing composite bodies variously obtained according to the temperature conditions of 400° C. and 500° C.

As shown in FIG. 3(a), when calcined at a relatively low temperature of 400° C., less aggregation between particles occurred and a single crystal particle having a very small size of approximately 3 nm was obtained. As shown in FIG. 3(b), when calcined at a temperature of 500° C., uniform particles having a size of approximately 5 to 7 nm were obtained.

Figure 4:
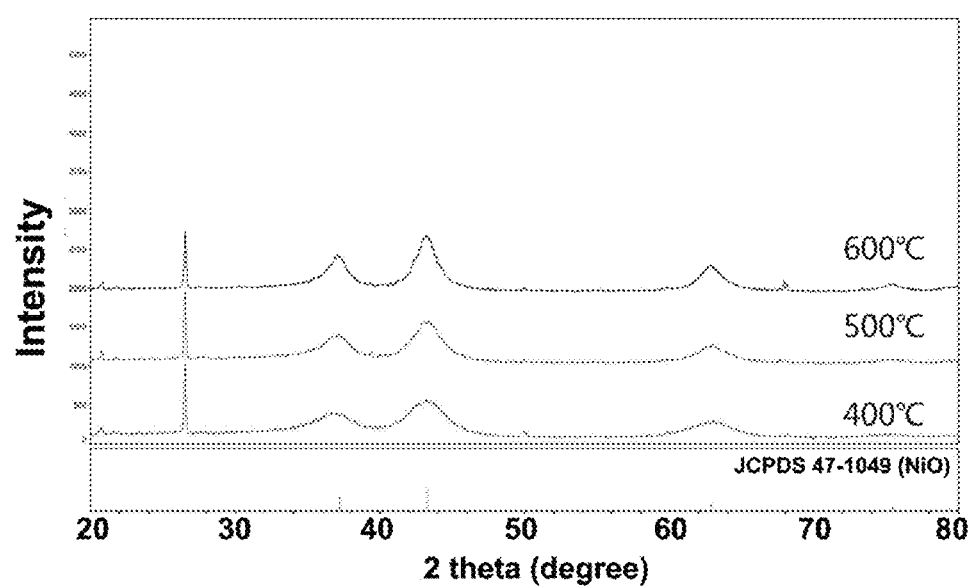
FIG. 4 is an XRD spectrum of a nickel/alumina/carbon-containing composite body based on the calcining temperature between 400 and 600° C. according to Example 1 of the present invention.

As a result of the analysis of the crystalline phase of the catalyst through the XRD spectrum, it could be confirmed from FIG. 4 that the crystalline phase NiO (JCPDS No. 47-1049) and a peak of nickel oxide exactly matched and that due to the influence on the calcination temperature, particles were aggregated while increasing to a high temperature. The size of the single crystal region was increased and thus a sharp peak appeared on the spectrum.

The content of nickel and aluminum elements was analyzed through ICP-AES (inductively coupled plasma atomic emission spectroscopy). As a result, for the samples calcined at 400° C., the content of Ni was 35.5 wt % and the content of Al was 11.4 wt %. For the sample calcined at 500° C., the content of Ni was 36.8 wt % and the content of Al was 9.4 wt %.

Comparative Example 1

Synthesis of a Carbon-Based Catalyst Supported with Nickel Excluding Alumina

The nickel/carbon composite catalyst was prepared in the same synthesis procedure as in Example 1 except for aluminum nitride hydrate ($Al(NO_3)_3 \cdot 9H_2O$) which acts as a support upon initial infiltration.

Figure 5:
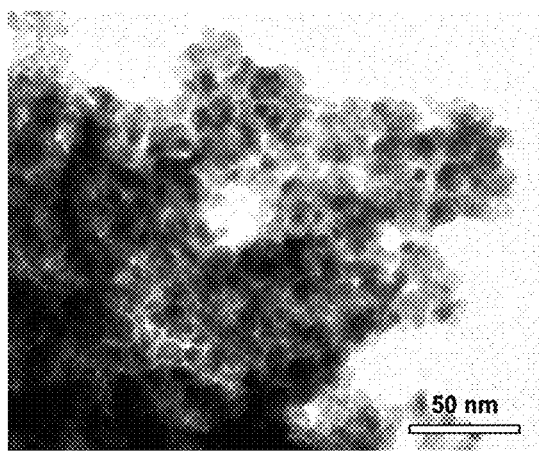
FIG. 5 is TEM images of a nickel oxide/carbon-containing composite body excluding alumina according to Comparative Example 1 (calcination at 500° C. for 4 hours) which is compared with Example 1 of the present invention.

In particular, as shown in the TEM image of FIG. 5 when calcined at a temperature of 500° C. for 4 hours, the particle size was, on average, three times greater than that of FIG. 3(b), while irregular particles having a size of 15 to 20 nm were obtained.

Figure 6:
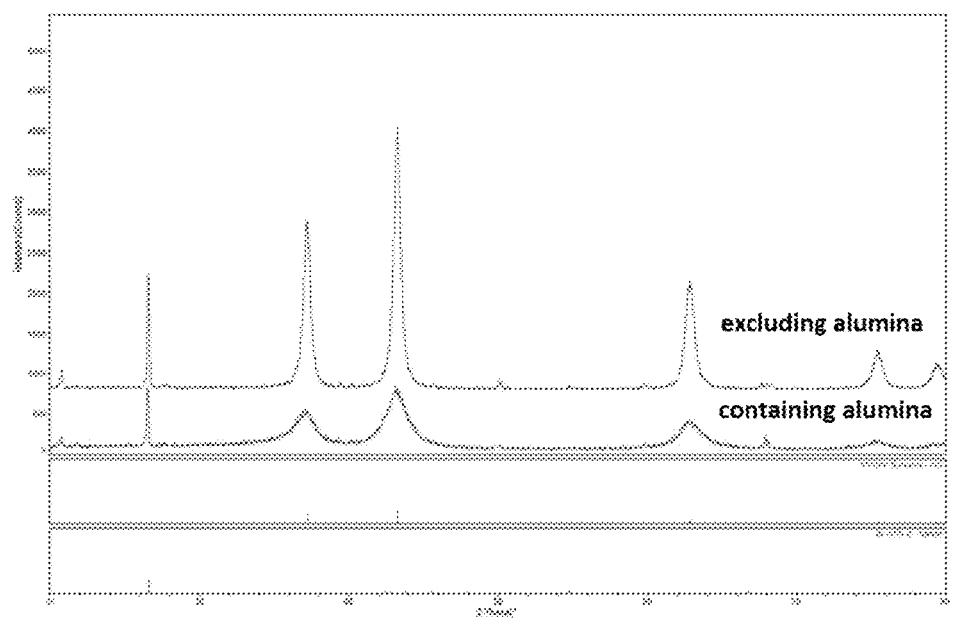
FIG. 6 is an XRD comparison spectrum of the nickel/alumina/carbon-containing composite body containing alumina (Example 1) and the composite body excluding alumina (Comparative Example 1) upon calcination at 600° C.

This tendency became larger as temperature increased. As seen in FIG. 6, upon calcination at a high temperature of 600° C., the catalyst containing alumina and the catalyst not containing alumina exhibited significantly different XRD peaks.

When alumina was not further used, aggregation between particles was large and thus much a stronger peak was observed. It could be seen from this peak that the size of the single crystal particle calculated from the Debye-Scherrer formula was significantly increased by 5 nm to 17 nm as compared with the catalyst containing alumina.

Example 2

Synthesis of a Carbon-Based Catalyst in which Iron is Supported on Alumina 3.58 g of $Fe(NO_3)_3 \cdot 9H_2O$ (Aldrich ACS reagent, ≥98%, m.p.=47° C., fw=404 g/mol) salt and 3.65 g of $Al(NO_3)_3 \cdot 9H_2O$ (Aldrich ACS reagent, ≥98%, m.p.=72.0° C., fw=375.13 g/mol) salt were uniformly ground along with 5.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 70° C., stored for 24 hours and melt-infiltrated.

After aging for 24 hours, the mixed powder was cooled and dried at room temperature. Heat treatment was then conducted in a calcination oven in an air atmosphere at 400 to 600° C. for 4 hours, to remove excess carbon and decompose the infiltrated metal hydrate salt. Accordingly, it was possible to obtain the iron/alumina/carbon-containing composite body supported with $Fe_2O_3$.

Figure 7:
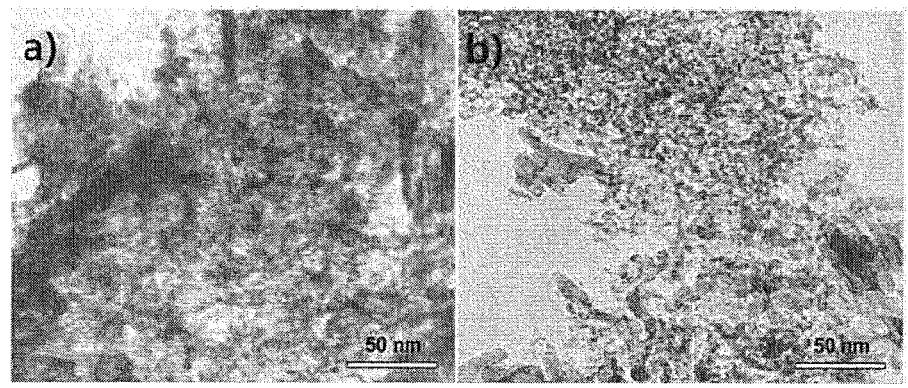
FIG. 7 is TEM images of a nickel/alumina/carbon-containing composite body by calcination temperature according to Example 2 of the present invention (a) calcination at 400° C. for 4 hours, and (b) calcination at 500° C. for 4 hours.

FIG. 7 is TEM images of the iron/alumina/carbon-containing composite bodies variously obtained according to the calcination temperature conditions of 400° C. and 500° C.

As shown in FIGS. 7(a) and (b), it was observed that, when calcined at 400° C. and 500° C., less aggregation between particles occurred and iron oxide particles having a size of approximately 2 to 3 nm were obtained, and amorphous alumina particles were slightly irregularly formed at a level of approximately 10 nm.

Figure 8:
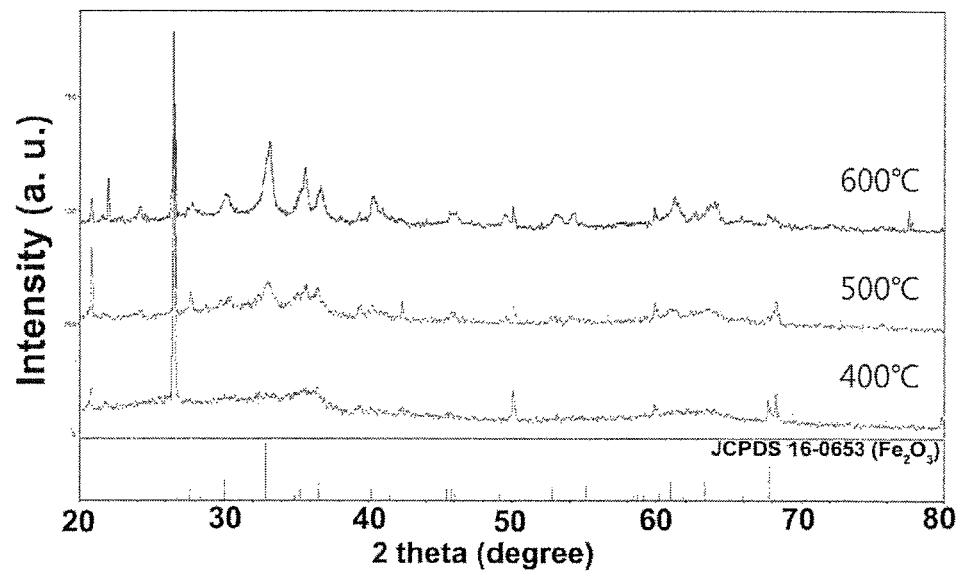
FIG. 8 is an XRD spectrum of an iron/alumina/carbon-containing composite body based on the calcination temperature between 400 and 600° C. according to Example 2 of the present invention.

The analysis of the crystalline phase was conducted through the XRD spectrum. The results showed from FIG. 8 that the crystalline phase of iron oxide $Fe_2O_3$ (JCPDS No. 16-0653) and a peak exactly matched and that due to the influence on the calcination temperature, particles were aggregated while increasing to a high temperature. The size of the single crystal region was increased and thus a sharp peak appeared on the spectrum.

Example 3

Synthesis of a Carbon-Based Catalyst in which Cobalt is Supported on Alumina 3.98 g of $Co(NO_3)_2 \cdot 6H_2O$ (Aldrich ACS reagent, ≥98%, m.p.=55° C., fw=291.03 g/mol) salt and 3.65 g of $Al(NO_3)_3 \cdot 9H_2O$ (Aldrich ACS reagent, ≥98%, m.p.=72.8° C., fw=375.13 g/mol) salt were uniformly ground along with 5.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 70° C., stored for 24 hours and melt-infiltrated.

After aging for 24 hours, the mixed powder was cooled and dried at room temperature. Heat treatment was then conducted in a calcination oven in an air atmosphere at 400 to 600° C. for 4 hours, to remove excess carbon and decompose the infiltrated metal hydrate salt. Accordingly, the cobalt/alumina/carbon-containing composite body supported with $Co_3O_4$ could be obtained.

Figure 9:
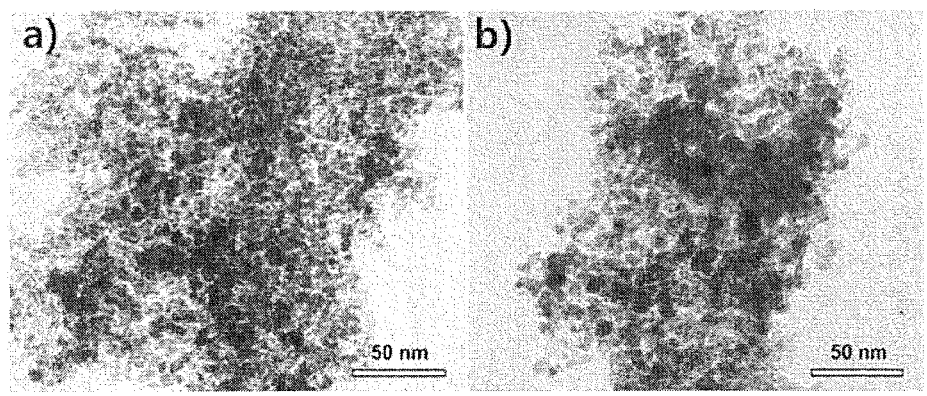
FIG. 9 is TEM images of a cobalt/alumina/carbon-containing composite body according to Example 3 of the present invention (a) calcination at 400° C. for 4 hours, and (b) calcination at 500° C. for 4 hours.

FIG. 9 is TEM images of the cobalt/alumina/carbon-containing composite bodies variously obtained according to the calcination temperature conditions of 400° C. and 600° C.

As shown in FIG. 9(a), it was observed that, when subjecting to calcination at a relatively low temperature of 400° C., less aggregation between particles occurred and relatively small single crystal particles having a particle size of about 10 nm were obtained. When subjecting to calcination at a relatively high temperature of 500° C., small particles having a particle size of about 10 nm were obtained as shown in FIG. 9(b).

Figure 10:
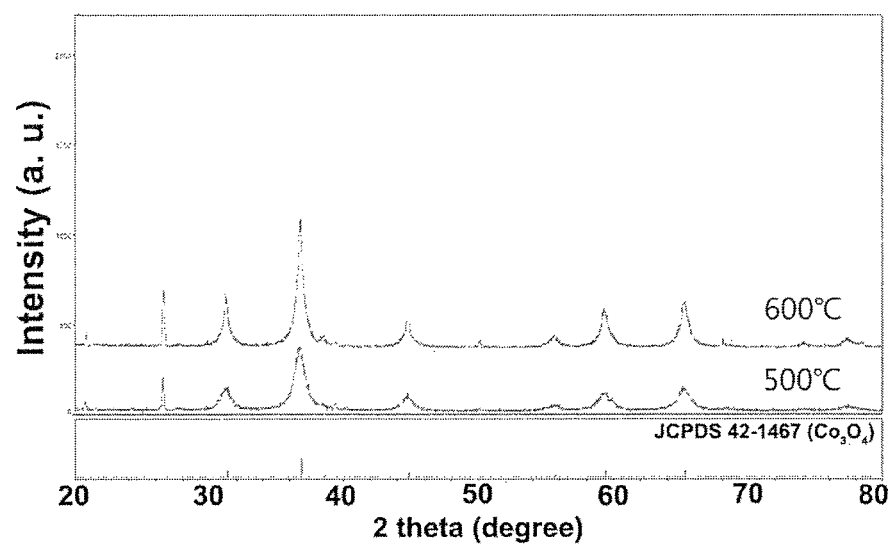
FIG. 10 is an XRD spectrum of the cobalt/alumina/carbon-containing composite body by calcination temperature according to Example 3 of the present invention.

As a result of the analysis of the crystalline phase of the catalyst through the XRD spectrum, it could be confirmed from FIG. 10 that the crystalline phase of cobalt oxide $Co_3O_4$ (JCPDS No. 42-1467) and a peak matched and that due to the influence on the calcination temperature, particles were aggregated while increasing to a high temperature. The size of the single crystal region was increased and thus a sharp peak appeared on the spectrum.

Example 4

Synthesis of a Carbon-Based Catalyst in which Cobalt is Supported on Alumina Using Activated Carbon as a Carbon Template As one of the candidates of the other carbon templates, commercial activated charcoal (STREM powder) was used. The analysis of the surface area and pores was conducted and the results showed that the value of the specific surface area was 1381 $m^2/g$ and the pore volume was 0.79 $cm^3/g$.

For the preparation of the catalyst, 3.70 g of $Co(NO_3)_2 \cdot 6H_2O$ (Aldrich ACS reagent, ≥98%, m.p.=55° C., fw=291.03 g/mol) salt and 3.40 g of $Al(NO_3)_3 \cdot 9H_2O$ (Aldrich ACS reagent, ≥98%, m.p.=72.8° C., fw=375.13 g/mol)

salt were uniformly ground along with 5.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 70° C., stored for 24 hours and melt-infiltrated.

After aging for 24 hours, the mixed powder was cooled and dried at room temperature. Heat treatment was then conducted in a calcination oven in an air atmosphere at 400 to 600° C. for 4 hours, to remove excess carbon and decompose the infiltrated metal hydrate salt. Accordingly, the cobalt/alumina/carbon-containing composite body supported with $Co_3O_4$ could be obtained.

Figure 11:
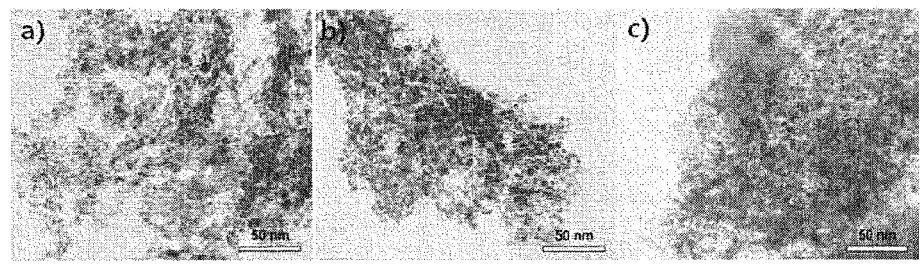
FIG. 11 is TEM images of a cobalt/alumina/carbon-containing composite body by calcination temperature when using activated carbon according to Example 4 of the present invention (a) calcination at 400° C. for 4 hours, (b) calcination at 500° C. for 4 hours, and (c) calcination at 600° C. for 4 hours.
Figure 12:
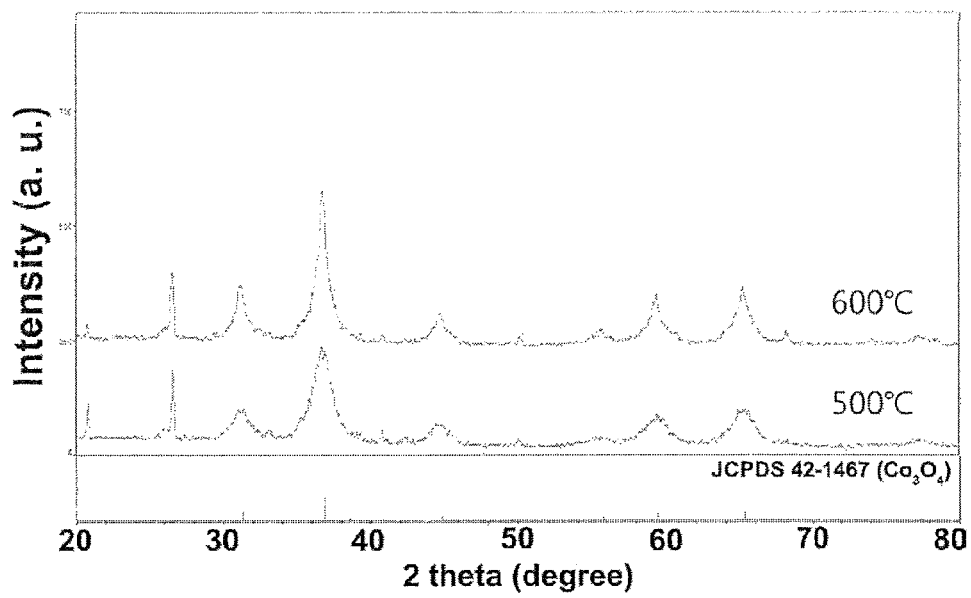
FIG. 12 is an XRD spectrum of the cobalt/alumina/carbon-containing composite body by calcination temperature according to Example 4 of the present invention.

FIGS. 11(a), 11(b) and 11(c) are TEM images of the cobalt/alumina/carbon-containing composite bodies variously obtained according to the calcination temperature conditions of 400° C. to 600° C.

The result of the TEM analysis showed that the cobalt/alumina/carbon-containing composite body was obtained at a level of a particle size similar to when activated charcoal was used as a support and that the size of active particles in FIG. 11(c) obtained by subjecting to calcination at a high temperature of 600° C. was larger than the particle size in FIG. 11(a) obtained by subjecting to calcination at a temperature of 400° C.

The analysis of the crystalline phase was conducted through the XRD spectrum, and the results showed from FIG. 10 that the crystalline phase of cobalt oxide $Co_3O_4$ (JCPDS No. 42-1467) and a peak matched and that the single crystal size of cobalt oxide particles by temperature was similar to when using activated charcoal.

Example 5

Synthesis of a Carbon-Based Catalyst in which Iron is Supported on Zirconia 3.58 g of $Fe(NO_3)_3.9H_2O$ (Aldrich ACS reagent, ≥98%, m.p.=47° C., fw=404 g/mol) salt and 6.795 g of $ZrO(NO_3)_2.6H_2O$ (Aldrich, fw=339.25 g/mol) salt were uniformly ground along with 10.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 60° C., stored for 24 hours and melt-infiltrated.

After aging for 24 hours, the mixed powder was cooled and dried at room temperature. Heat treatment was then conducted in a calcination oven in an air atmosphere at 500° C. for 4 hours, to remove excess carbon and decompose the infiltrated metal hydrate salt. Accordingly, it was possible to obtain the iron/zirconia/carbon-containing composite body supported with $Fe_2O_3$.

Figure 13:
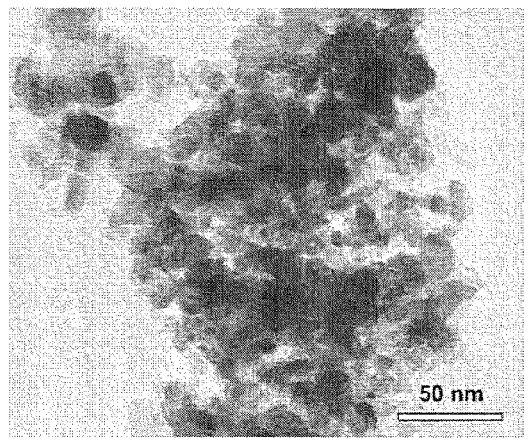
FIG. 13 is a TEM images of the iron/zirconia/carbon-containing composite body according to Example 5 of the present invention (calcination at 500° C. for 4 hours).
Figure 14:
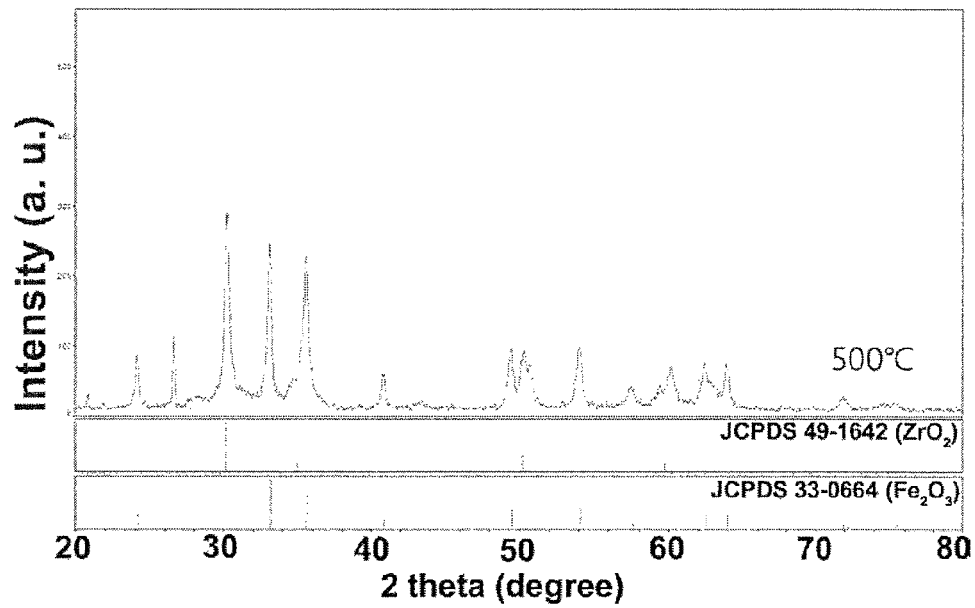
FIG. 14 is an XRD spectrum of an iron/zirconia/carbon-containing composite body upon calcination at 500° C. according to Example 5 of the present invention.

FIG. 13 is a TEM image of the iron/zirconia/carbon-containing composite body obtained through the calcination process at 500° C. Overall, the size of the particles was somewhat unevenly obtained as 10 to 20 nm. Further, the analysis of the crystalline phase was conducted through an XRD spectrum. The results showed from FIG. 14 that the crystalline phase of iron oxide $Fe_2O_3$ (JCPDS No. 33-0664) and the crystalline phase of zirconia $ZrO_2$ (JCPDS No. 49-1642) appeared together.

Also, it was found by the XRD analysis that the particles were not alloy forms and that iron oxide and zirconia particles had been separately irregularly formed.

Example 6

Synthesis of a Carbon-Based Catalyst in which Iron and Cobalt are Supported Together 3.98 g of $Co(NO_3)_2.6H_2O$ (Aldrich ACS reagent, ≥98%, m.p.=55° C., fw=291.03 g/mol) salt and 3.58 g of $Fe(NO_3)_3$ $9H_2O$ (Aldrich ACS reagent, ≥98%, m.p.=47° C., fw=404 g/mol) salt were uniformly ground along with 5.0 g of activated charcoal using a mortar and pestle.

Thereafter, the resulting mixed powder was placed in a polypropylene vessel with a capacity of 50 mL, after which the cap of the vessel was tightly shut and the vessel was placed in a drying oven at 60° C., stored for 24 hours and melt-infiltrated.

After aging for 24 hours, the mixed powder was cooled and dried at room temperature. Heat treatment was then conducted in a calcination oven in an air atmosphere at 500° C. for 4 hours, to remove excess carbon and decompose the infiltrated metal hydrate salt. Accordingly, the carbon composite catalyst support supported with iron and cobalt could be obtained.

Figure 15:
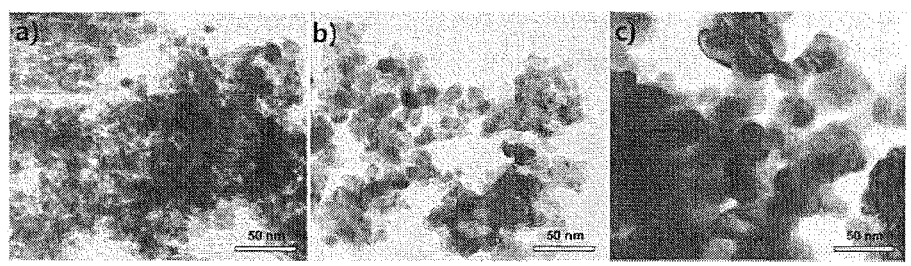
FIG. 15 is TEM images of an iron oxide/cobalt oxide/carbon-containing composite body by calcination temperature according to Example 6 of the present invention (a) calcination at 400° C. for 4 hours, (b) calcination at 500° C. for 4 hours, and c) calcination at 600° C. for 4 hours.

FIGS. 15(a), 15(b) and 15(c) are TEM images of the cobalt/iron oxide/carbon-containing composite body variously obtained according to the calcination temperature conditions of 400° C. to 600° C.

As shown in FIG. 15(a), it was observed that, when calcined at a relatively low temperature of 400° C., less aggregation between particles occurred and single crystal particles having a relatively small size of approximately 12 nm were obtained. On the other hand, as shown in FIGS. 15(b) and 15(c), when calcined at high temperatures of 500° C. and 600° C., the sizes of the single particles increased to the level of 17 nm and 30 nm, respectively.

Although the forgoing is described with reference to the preferred embodiments of the present invention, it will be appreciated by those of ordinary skill in the art that various changes and modifications can be made to the present invention without departing from the spirit and scope of the invention as set forth in the claims below and that such modifications and changes are within the scope of the claims.

The invention claimed is:

1. A method for preparing a composite body in which first size-controlled metal-containing particles and second size-controlled metal-containing particles are supported on a carbon material or connected by a carbon material, the method comprising the following steps:
   a first step of mixing a first metal hydrate salt forming a first metal oxide, a second metal hydrate salt forming a second metal oxide, and a porous carbon material particle;
   a second step of melt-infiltrating the first metal hydrate salt and the second metal hydrate salt in the pores of the porous carbon material particle at a temperature that can melt the first metal hydrate salt and the second metal hydrate salt;
   optionally, a third step of drying the porous carbon material particles in which the first metal hydrate salt and the second metal hydrate salt are melt-infiltrated;
   a fourth step of subjecting the resultant carbon material particles to high temperature calcination at a temperature and condition that thermally decompose the first metal hydrate salt, the second metal hydrate salt and the porous carbon material, thereby forming the first metal oxide particles and the second metal oxide particles in which the particle sizes are controlled by the pores of the porous carbon material, while forming a composite body in which the first metal oxide particles and the second metal oxide particles are supported or connected by the carbon material remaining after the thermal decomposition of the porous carbon material; and optionally, a fifth step of chemically changing the first metal oxide particles, the second metal oxide particles or both of them to the first metal-containing particles or the second metal-containing particles.

2. The method for preparing a composite body according to claim 1 wherein in the fourth step, the first metal oxide particles are separated by the second metal oxide particles, thus inhibiting the first metal oxide particles from sintering.

3. The method for preparing a composite body according to claim 1 wherein a reduction potential of the second metal oxide is higher than a reduction potential of the first metal oxide, and in the fifth step the whole or a surface of the first metal oxide particle is reduced to the first metal by a reduction reaction.

4. The method for preparing a composite body according to claim 1 wherein, in the first step, the porous carbon material particles have an average size of 200 nm to 0.2 μm.

5. The method for preparing a composite body according to claim 1 wherein, in the first step, the porous carbon material particles have an average pore size of 2 to 50 nm.

6. The method for preparing a composite body according to claim 1 wherein, in the first step, the porous carbon material particles have a pore volume of 0.3 cm 3/g or more.

7. The method for preparing a composite body according to claim 1 wherein, in the fourth step, the first metal oxide particles and the second metal oxide particles, each independently, have an average particle size of 2 to 30 nm.

8. The method for preparing a composite body according to claim 1 wherein, in the fourth step, the second metal oxide particles are amorphous.

9. The method for preparing a composite body according to claim 1 wherein, in the fourth step, the second metal oxide particles are selected from the group consisting of silica, alumina, titania, zirconia and a mixture thereof.

10. The method for preparing a composite body according to claim 1 wherein in the fourth step, the high temperature calcination is conducted at a temperature of 300 to 650° C.

11. The method for preparing a composite body according to claim 1 wherein the first metal hydrate salt and the second metal hydrate salt have, each respectively, a melting point between 30 and 100° C.

12. The method for preparing a composite body according to claim 1 wherein the first metal hydrate salt is selected from the group consisting of $Cr(NO_3)_3.9H_2O$, $Fe(NO_3)_3.9H_2O$, $Co(NO_3)_2.6H2O$, $Ni(NO_3)_2.6H_2O$, $Pd(NO_3)_2.2H_2O$, $FeCl_3.6H_2O$, $CoCl_2.6H_2O$, $CuCl_2.2H_2O$, $Cr_2(SO_4)_3.12H_2O$, $FeSO_4.7H_2O$, $CoSO_4.7H_2O$, and $NiSO_4.6H_2O$.

13. The method for preparing a composite body according to claim 1 wherein the second metal hydrate salt is selected from the group consisting of $Mg(NO_3)_2.6H_2O$, $Al(NO_3)_3.9H_2O$, $Zn(NO_3)_2.3H_2O$, $Zn(NO_3)_2.6H_2O$, $MnCl_2.4H_2O$, $Al_2(SO_4)_3.18H_2O$, $ZnSO_4.6H_2O$, and $ZrO(NO_3)_2.6H_2O$.

14. The method for preparing a composite body according to claim 1 wherein the porous carbon material is selected from the group consisting of activated carbon, activated charcoal, synthetic porous carbon support CMK and a mixture thereof.

15. The method for preparing a composite body according to claim 1 wherein the first metal hydrate salt and the second metal hydrate salt are infiltrated in an amount of 0.3 to 3 grams based on the carbon unit gram thereof, in consideration of the density of each metal salt and the pore volume of the porous carbon material.

16. The method for preparing a composite body according to claim 1 wherein the first step of mixing the first metal hydrate salt, the second metal hydrate salt and the porous carbon material particles is conducted by mechanically grinding them.

17. A composite body, prepared by the method defined in claim 1, in which first metal-containing particles and second metal-containing particles are supported on a carbon material or connected by a carbon material, wherein the first metal-containing particles are maintained at intervals between the particles by the second metal-containing particles and the carbon material, and the first metal-containing particles are contained in an amount of 10 to 50% by weight, the second metal-containing particles are in an amount of 10 to 50% by weight, and the residual carbon material is contained in an amount of 20 to 60% by weight, based on the total amount of the composite body.

18. The composite body according to claim 17 wherein the first metal-containing particles exhibit a catalytic activity and the second metal-containing particles are inert to the catalytic reaction.

19. The composite body according to claim 17 wherein the first metal-containing particles are those in which the surface or the whole of the first metal oxide particles are reduced to a first metal.

20. The composite body according to claim 17 wherein the first metal-containing particles are a crystalline form having a grid structure, and the second metal-containing particles are amorphous.

* * * * *